United States Patent
Matsumoto et al.

(10) Patent No.: US 7,507,812 B2
(45) Date of Patent: *Mar. 24, 2009

(54) PROCESS FOR PRODUCING 3-CHLOROMETHYL-3-CEPHEM DERIVATIVES

(75) Inventors: Nobuo Matsumoto, Tokyo (JP); Hiroshi Kawakabe, Tokyo (JP); Yasuko Manabe, Tokyo (JP)

(73) Assignee: Nippon Chemical Industrial Co., Ltd., Tokyo (JP)

( * ) Notice: Subject to any disclaimer, the term of this patent is extended or adjusted under 35 U.S.C. 154(b) by 461 days.

This patent is subject to a terminal disclaimer.

(21) Appl. No.: 10/570,248

(22) PCT Filed: Sep. 6, 2004

(86) PCT No.: PCT/JP2004/012925

§ 371 (c)(1),
(2), (4) Date: Mar. 2, 2006

(87) PCT Pub. No.: WO2005/026176

PCT Pub. Date: Mar. 24, 2005

(65) Prior Publication Data

US 2007/0027313 A1 Feb. 1, 2007

(30) Foreign Application Priority Data

Sep. 9, 2003 (JP) .............................. 2003-316386

(51) Int. Cl.
*C07D 501/08* (2006.01)
(52) U.S. Cl. ...................................................... 540/215
(58) Field of Classification Search .................. 540/215
See application file for complete search history.

(56) References Cited

U.S. PATENT DOCUMENTS

| | | | |
|---|---|---|---|
| 3,536,698 A | 10/1970 | Chauvette et al. | |
| 3,975,385 A | 8/1976 | Bouchaudon et al. | |
| 4,401,668 A | 8/1983 | Lunn | |
| 4,486,586 A | 12/1984 | Narita et al. | |
| 4,566,996 A | 1/1986 | Torii et al. | |
| 4,686,216 A | 8/1987 | Angerbauer et al. | |
| 5,132,419 A | 7/1992 | Lanz et al. | |
| 7,157,574 B2 * | 1/2007 | Matsumoto et al. | 540/215 |

FOREIGN PATENT DOCUMENTS

| | | |
|---|---|---|
| EP | 0 963 989 A | 12/1999 |
| GB | 1271180 A | 4/1972 |
| GB | 1454587 A | 11/1976 |
| GB | 1454588 A | 11/1976 |
| GB | 2099817 A | 12/1982 |
| JP | 49-39277 B | 10/1974 |
| JP | 50-52085 A | 5/1975 |
| JP | 50-52086 A | 5/1975 |
| JP | 50-52088 A | 5/1975 |
| JP | 58-72591 A | 4/1983 |
| JP | 58-74689 A | 5/1983 |
| JP | 59-134779 A | 8/1984 |
| JP | 59-172493 A | 9/1984 |
| JP | 60-255796 A | 12/1985 |
| JP | 61-5084 A | 1/1986 |
| JP | 1-156984 A | 6/1989 |
| JP | 1-308287 A | 12/1989 |
| JP | 3-120288 A | 5/1991 |
| JP | 2004-2451 A | 1/2004 |
| WO | WO 99/10352 A | 3/1999 |

OTHER PUBLICATIONS

Taniguch, M. et al., "Development and Industrialization of New Intermediates 3-Chloromethyl-Δ3-Cephems for Cephalosporin Antibiotic Synthesis", Nippon Kagakukaishi, 1995, pp. 577-587, No. 8, the Chemical Society of Japan.

* cited by examiner

*Primary Examiner*—Mark L Berch
(74) *Attorney, Agent, or Firm*—Smith Patent Office

(57) ABSTRACT

An industrially advantageous process for producing 3-chloromethyl-3-cephem derivative crystals. The process for 3-chloromethyl-3-cephem derivative production comprises: a first step in which a thiazolineazetidinone derivative (1) is reacted with a sulfonyl halide (2) in the presence of an acid in a solvent to obtain an azetidinone derivative (3); a second step in which the azetidinone derivative (3) is reacted with a chlorinating agent in an organic solvent to obtain a chlorinated azetidinone derivative (4); and a third step in which the chlorinated azetidinone derivative (4) is reacted with an alcoholate (5) at a pH of 8 or lower in a solvent comprising an alcohol and an ether and a 3-chloromethyl-3-cephem derivative (6) is recovered in the form of crystals.

9 Claims, No Drawings

PROCESS FOR PRODUCING 3-CHLOROMETHYL-3-CEPHEM DERIVATIVES

BACKGROUND OF THE INVENTION

1. Field of the Invention

The present invention relates to a process for preparing 3-chloromethyl-3-cefem derivatives expressed by Chemical Formula (6), which are useful as intermediates for synthesizing 3-chloromethyl-3-cephem antibiotics:

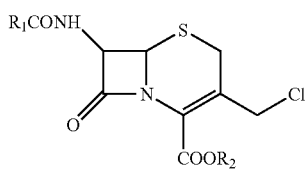

(6)

wherein $R_1$ and $R_2$ each represent an aromatic hydrocarbon group.

2. Description of the Related Art

The 3-chloromethyl-3-cefem derivatives expressed by Chemical Formula (6) are known as useful intermediates for synthesizing cephalosporin antibiotics, as disclosed in, for example, Japanese Unexamined Patent Application Nos. 59-172493, 58-72591, 60-255796, 61-5084, 1-156984, 1-308287.

For the preparation of a 3-chloromethyl-3-cephem derivative expressed by Chemical Formula (6), for example, a technique is disclosed in Development and Industrialization of New Intermediates 3-Chloromethyl-Δ3-Cephems for Cephalosporin Antibiotic Synthesis (Taniguchi et al., NIPPON KAGAKUKAISHI, No. 8, 577-587, 1995).

In particular, for the preparation of a 3-chloromethyl-3-cefem derivative expressed by Chemical Formula (9) from a chlorinated azetidinone derivative expressed by Chemical Formula (8), for example, Japanese Unexamined Patent Application No. 58-74689 has disclosed a process in which the chlorinated azetidinone derivative expressed by Chemical Formula (8) is allowed to react in an organic solvent in the presence of a base according to Reaction Formula (1).

Reaction Formula(1)

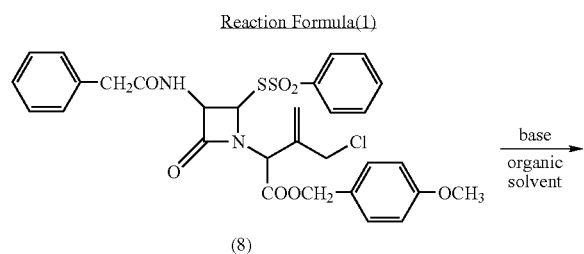

(8)

→ base / organic solvent

-continued

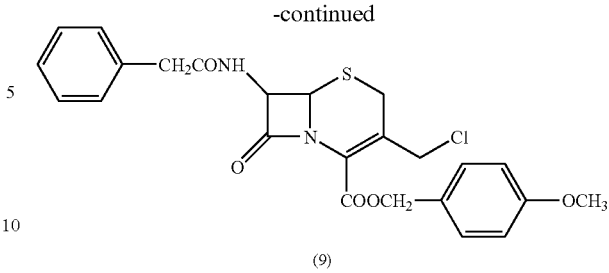

(9)

However, the process proposed by Japanese Unexamined Patent Application No. 58-74689 provides 3-chloromethyl-3-cefem derivatives in an oil form. In this process, dimethylformamide, which dissolves both the starting material, an azetidinone derivative (Chemical Formula (8)), and the reaction product, a 3-chloromethyl-3-cephem derivative (Chemical Formula (9)), is used as a reaction solvent, and the starting material is allowed to react with a base, weak alkaline ammonia or ammonia water, while the reaction product is prevented from being decomposed.

In this process, an alcohol, such as methanol, ethanol, or 2-propanol, may be used as the reaction solvent, and a metal hydroxide, such as strongly basic sodium hydroxide or potassium hydroxide, may be used as the base. However, since the alcohol does not dissolve the reaction product, the 3-chloromethyl-3-cephem derivative, the use of the alcohol does not provide the reaction product in an oil form. In addition, the alcohol reacts with the base to produce water, which dissolves the base to increase the pH of the reaction system, that is, to make the reaction system alkaline. Consequently, the reaction product, the 3-chloromethyl-3-cephem derivative, is decomposed by the alkali and thus the yield is reduced.

Furthermore, 3-chloromethyl-3-cephem derivatives each include a high reaction activity chlorine atom in its molecule, and are, consequently, instable in an oil form. For example, the 3-chloromethyl-3-cephem derivatives release hydrochloric acid which causes self decomposition of the derivatives during storage at room temperature, thus degrading the quality.

Accordingly, a 3-chloromethyl-3-cephem derivative is desired that is relatively stable for a long time in moderate conditions.

A process has been proposed in which a crystalline 3-chloromethyl-3-cephem derivative is prepared.

For example, International Patent Application No. WO 99/10352 has proposed a process for preparing a crystalline 3-chloromethyl-3-cephem derivative by crystallizing an oily 3-chloromethyl-3-cephem derivative dissolved in dimethylformamide, with a solvent containing a cold alcohol.

However, this process includes a complicated step of crystallizing an oily 3-chloromethyl-3-cephem derivative that has once been synthesized, and is thus disadvantageous in industrial production.

Since a process for industrially preparing a crystalline 3-chloromethyl-3-cephem derivative expressed by Chemical Formula (6) includes a series of steps each using an expensive raw material, it is desired to recycle reaction by-products. In view of the above-mentioned disadvantages, therefore, the development of a series of preparing steps is required.

SUMMARY OF THE INVENTION

Accordingly, an object of the present invention is to provide an industrially advantageous process for preparing a crystalline 3-chloromethyl-3-cephem derivative useful as an intermediate for synthesizing cephalosporin antibiotics, the process being capable of providing a highly pure crystalline 3-chloromethyl-3-cephem derivative with high yield using a simple process, and capable of recycling a by-product, such as a sulfinic acid metal salt, produced in a reaction.

In view of the above-described disadvantages, the inventors discovered a series of continuous reaction steps including first to third steps in which in the third step, a chlorinated azetidinone derivative produced in the second step and an alcoholate are used as raw materials, and a combination of solvents, i.e., an alcohol not dissolving the reaction product, the crystalline 3-chloromethyl-3-cephem derivative, and a solvent dissolving the chlorinated azetidinone derivative being a staring material and impurities such as byproducts is used as a reaction solvent.

Specifically, it was found that a 3-chloromethyl-3-cephem derivative expressed by Chemical Formula (6) can be provided as a crystal by the above reaction system in the absence of water at pH controlled in a specified range. Furthermore, the inventors discovered that sulfonyl halide, which is produced by reaction of a sulfinic acid metal salt with a halogen, can be recycled as a raw material of the first step. The sulfinic acid metal salt is produced as a byproduct in the third step, separated from the crystalline 3-chloromethyl-3-cephem derivative by solid-liquid separation, and precipitated by a specified operation of a mother liquid containing the sulfinic acid metal salt.

A first aspect of the present invention provides a process for producing a 3-chloromethyl-3-cephem derivative including the following first to third steps:

First step: An azetidinone derivative is prepared by a reaction of a thiazoline azetidinone derivative with a sulfonyl halide in a solvent and in the presence of an acid.

The thiazoline azetidinone derivative is expressed by Chemical Formula (1):

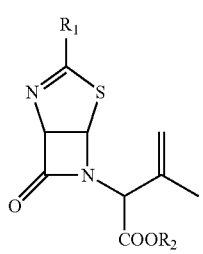

(1)

wherein $R_1$ and $R_2$ each represent an aromatic hydrocarbon group.

The sulfonyl halide is expressed by Chemical Formula (2):

$$R_3\text{—}SO_2X \quad (2)$$

wherein, $R_3$ represents one selected from the group consisting of substituted or unsubstituted aryl groups and substituted or unsubstituted heterocyclic residues, and X represents a halogen atom.

The azetidinone derivative is expressed by Chemical Formula (3):

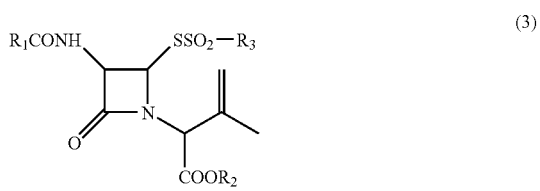

(3)

wherein $R_1$, $R_2$ and $R_3$ are the same as described above.

Second step: A chlorinated azetidinone derivative is prepared by a reaction of the azetidinone derivative obtained by the first step with a chlorination agent in an organic solvent.

The chlorinated azetidinone derivative is expressed by Chemical Formula (4):

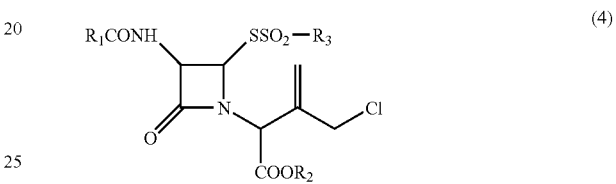

(4)

wherein $RR_1$, $R_2$ and $R_3$ are the same as described above.

Third step: A 3-chloromethyl-3-cefem derivative in a crystal form is prepared by a reaction of the chlorinated azetidinone derivative obtained by the second step with an alcoholate expressed by Chemical Formula (5) in a solvent containing an alcohol and an ether at a pH of 8 or less.

The alcoholate is expressed by Chemical Formula (5):

$$R_4\text{—}OM \quad (5)$$

wherein $R_4$ represents an organic group and M represents an alkaline metal atom.

The 3-chloromethyl-3-cefem derivative is expressed by Chemical Formula (6):

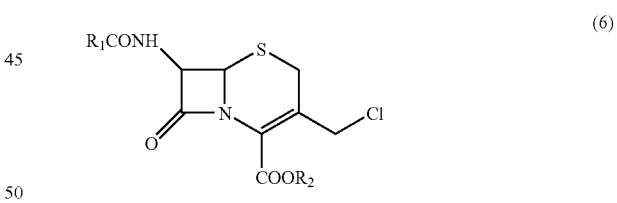

(6)

wherein $R_1$ and $R_2$ are the same as described above.

A second aspect of the present invention provides a process for producing a 3-chloromethyl-3-cephem derivative including fourth and fifth steps of preparing a sulfonyl halide from a metal sulfinate obtained by the third step after a 3-chloromethyl-3-cephem derivative in a crystal form is recovered by the first to third steps of the above-described process, so that the sulfonyl halide is used as a raw material of the first step to perform the first to third steps.

Fourth step: A metal sulfinate is recovered from a mother liquid of the reaction solution obtained by the third step.

The metal sulfinate is expressed by Formula (7):

$$R_3\text{—}SO_2M \quad (7)$$

wherein $R_3$ and M are the same as described above.

Fifth step: A sulfonyl halide is prepared by a reaction of the metal sulfinate recovered in the fourth step with a halogen in an organic solvent.

The sulfonyl halide is expressed by Chemical Formula (2);

$$R_3\text{—}SO_2X \quad (2)$$

wherein $R_3$ is the same as described above.

DESCRIPTION OF THE PREFERRED EMBODIMENTS

The present invention will now be described in detail with reference to preferred embodiments.

The present invention provides a process for producing a 3-chloromethyl-3-cephem derivative including the following first step to third step:

First Step:

The first step is to perform a reaction of a thiazoline azetidinone derivative (Compound (1)) with a sulfonyl halide (Compound (2)) in a solvent and in the presence of an acid to produce an azetidinone derivative (Compound (3)) according to the following Reaction Formula (2):

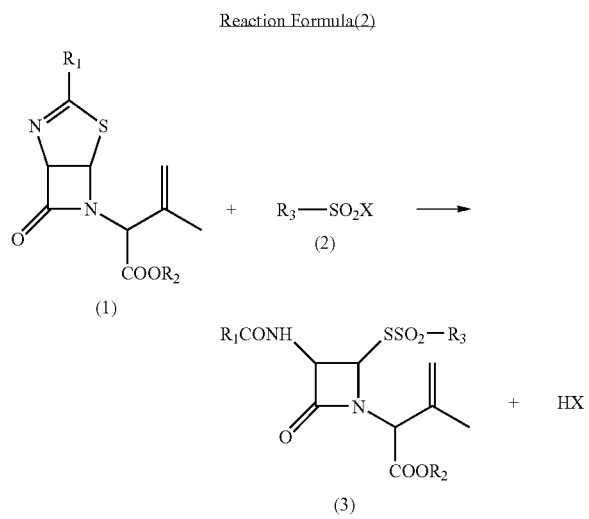

wherein $R_1$, $R_2$, and $R_3$ are the same as described above.

$R_1$ and $R_2$ in the formula of the starting material, the thiazoline azetidinone derivative (Compound (1)), used in the first step of the present invention each represent a substituted or unsubstituted aromatic hydrocarbon group, for example, benzyl, p-methoxybenzyl, phenyl, or p-tosyl. $R_1$ and $R_2$ may be the same or different.

The thiazoline azetidinone derivative, which is expressed by Chemical Formula (1), is a known chemical compound and easily obtainable in accordance with a production method disclosed in, for example, U.S. Pat. No. 3,536,698, Japanese Unexamined Patent Application Publication Nos. 50-52086, 50-52085, 50-52088, and 59-134779; and Japanese Examined Patent Application Publication No. 49-39277.

Another starting material, a sulfonyl halide, in the first step of the present invention is expressed by Chemical Formula (2) in which $R_3$ represents a substituted or unsubstituted aryl group or a substituted or unsubstituted heterocyclic residue.

$$R_3\text{—}SO_2X \quad (2)$$

Exemplary substituted or unsubstituted aryl groups include phenyl, p-methyphenyl, p-methoxyphenyl, p-nitrophenyl, p-chlorophenyl, and pentachlorophenyl. Exemplary substituted or unsubstituted heterocyclic residues include 2-pyridyl, 2-benzothiazolyl, 1,3,4-thiadiazol-5-yl, 2-methyl-1,3,4-thiadiazol-5-yl, 1,2,3,4-tetrazol-5-yl, 1-methyl-1,2,3,4-tetrazol-5-yl, and 1-phenyl-1,2,3,4-tetrazol-5-yl. In Formula (2), X represents a halogen atom, for example, chlorine, bromine, or iodine.

In this step, 1.0 to 5 and preferably 1.0 to 1.2 times moles of the sulfonyl halide (Compound (2)) is added per mole of the thiazoline azetidinone derivative (Compound (1)). This is due to the fact that when the amount of the sulfonyl halide is less than 1 time moles, the reaction does not completely finish, unreacted raw materials remain, and it is difficult to produce a highly pure compound. On the other hand, when the amount is more than 5 times moles, it is not preferable because a lot of sulfonyl halide remains and inhibits the crystallization of the thiazoline azetidinone derivative (Compound (1)) as the reaction proceeds. Thus, it becomes difficult to perform purification.

Exemplary acids to be used in the first step include mineral acids, such as hydrochloric acid, sulfuric acid, nitric acid, and perchloric acid; and organic acids, such as acetic acid, formic acid, and trifluoroacetic acid. These acids may be used alone or in combination. In this case, 0.1 to 10 and preferably 1.0 to 1.5 times moles of the acid is generally added per mole of thiazoline azetidinone derivative (Compound (1)).

Exemplary reaction solvents to be used in the first step include lower alcohols, such as methanol, ethanol, 1-propanol, and 2-propanol; ketones, such as acetone and methyl ethyl ketone; nitrites, such as acetonitrile and butyronitrile; ethers, such as diethyl ether, dibutyl ether, tetrahydrofuran, and dioxane; and lower nitroparaffins, such as nitromethane and nitroethane. These reaction solvents may be used alone or in combination. The reaction solvent can be mixed with another reaction solvent, such as dichloromethane, 1,2-dichloroethane, chloroform, carbon tetrachloride, benzene, chlorobenzene, ethyl acetate, or ethyl formate, to prepare a mixed solvent.

The reaction temperature should be set between −20 to 50° C. and preferably between 0 to 20° C., and the reaction time is preferably between 10 minutes to 2 hours.

After the reaction, the acid can be removed from the reaction solution by conventional means, such as water washing or neutralization with an alkaline solution. The reaction solution is then concentrated and purified by recrystallization with a solvent, such as n-hexane or the like according to need, whereby the azetidinone derivative (Compound (3)) is obtained.

Second Step:

The second step is to perform a reaction of the azetidinone derivative (Compound (3)) obtained by the first step with a chlorination agent in an organic solvent to produce a chlorinated azetidinone derivative (Compound (4)) according to the following Reaction Formula (3):

Reaction Formula(3)

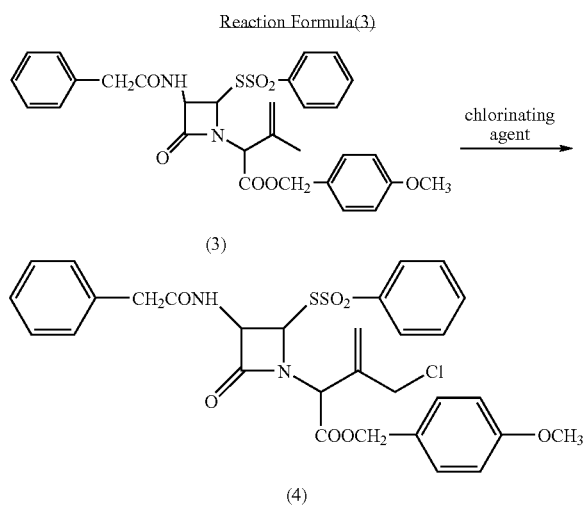

wherein $R_1$, $R_2$, and $R_3$ are the same as described above.

Exemplary chlorination agents to be used in the second step include t-BuOCl, HOCl, $Cl_2O$, Chlorine, $PCl_5$, and $SO_2Cl_2$. These chlorination agents may be used alone or in combination. The amount of the chlorination agent added is 1 to 7 times moles and preferably 1 to 3 times moles relative to the azetidinone derivative (Compound (3)) because the reaction can provide a highly pure chlorinated azetidinone derivative with a high yield. On the other hand, when the amount is less than 1 time moles, it is not preferable because unreacted raw materials are left. When the amount is more than 7 times moles, it is not preferable because a side reaction proceeds.

Exemplary reaction solvents to be used in the second step include halogenated hydrocarbons, such as chloroform, dichloroethane, and carbon tetrachloride; aromatic hydrocarbons, such as benzene and chlorobenzene; ethers, such as diethyl ether, dipropyl ether, diisopropyl ether, tetrahydrofuran, tetrahydropyran, dioxane, anisole, and phenetole; dialkoxyethanes, such as 1,2-dimethoxyetane, 1,2-diethoxyethane, 1,2-dibutoxyethane, 1,2-benzyloxyethane, and 1,2-diacetoxyethane; and esters, such as ethylformate, ethyl acetate, and ethoxyethyl acetate. These reaction solvents may be used alone or in combination.

If necessary, the reaction in the second step can be performed in the presence of a hydrogen chloride trapping agent. Exemplary hydrogen chloride trapping agents include hydroxides of alkaline metals, such as calcium, potassium, sodium, and lithium; carbonates, such as calcium carbonate, sodium carbonate, and potassium carbonate; bicarbonate, such as sodium bicarbonate, and potassium bicarbonate; epoxides, such as propylene oxide and butylenes oxide; and polyvinylpyridine. These hydrogen chloride trapping agents may be used alone or in combination. In the second step, 1 to 100 and preferably 1 to 30 times moles of the hydrogen chloride trapping agent is added per mole of the azetidinone derivative (Compound (3)).

The reaction temperature should be set between −70 to 70° C. and preferably between −10 to 40° C., and the reaction time is preferably between 0.5 to 24 hours and preferably between 2 to 8 hours.

After the reaction, the reaction product is recovered by an ordinary method. Namely, the product is extracted, washed with water, recrystallized, and purified by column chromatography or the like according to need, whereby the chlorinated azetidinone derivative (Compound (4)) is obtained. A concentrate containing the chlorinated azetidinone derivative (Compound (4)), which is prepared by concentrating the reaction solution after the reaction, can be directly used as a solution containing the raw material, the chlorinated azetidinone derivative, in the third step.

Third Step:

The third step is to recover a 3-chloromethyl-3-cephem derivative (Compound (6)) in a crystal form according to the following Reaction Formula (4).

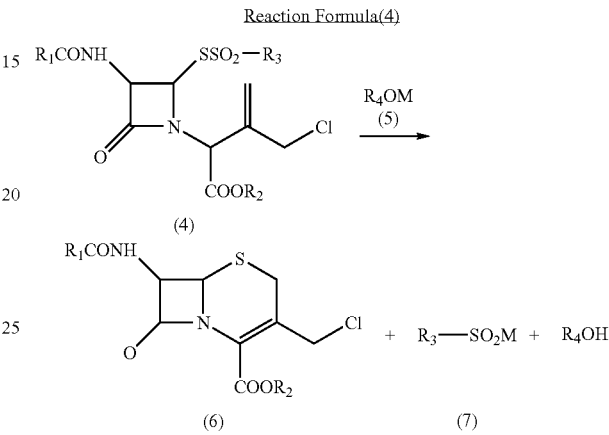

wherein $R_1$, $R_2$, and $R_3$ are the same as described above, $R_4$ is an organic group, and M is an alkaline metal atom. In the process, solution A containing the chlorinated azetidinone derivative in a solvent described later (hereinafter referred to as "solution A") and solution B containing an alcoholate in a solvent containing an alcohol (hereinafter referred to as "solution B") are added dropwise into solution C containing an alcohol (hereinafter referred to as "solution C"), followed by reaction at a pH of 8 or less and preferably at a pH of 6 to 8 to precipitate the 3-chloromethyl-3-cephem derivative (Compound (6)). After reaction, the 3-chloromethyl-3-cephem derivative can be recovered in a crystal form by solid-liquid separation.

Solution A:

In the present invention, solution A may be prepared by dissolving the chlorinated azetidinone derivative (Compound (4)) produced in the second step in a solvent so as to contain the chlorinated azetidinone derivative at a predetermined concentration.

Exemplary solvents used for dissolving the chlorinated azetidinone derivative include esters, such as methyl formate, ethyl formate, methyl acetate, ethyl acetate, butyl acetate, and ethyl propionate; ethers, such as diethyl ether, dipropyl ether, diisopropyl ether, tetrahydrofuran, tetrahydropyran, dioxane, anisole, and phenetole; dialkoxyethanes, such as 1,2-dibenzyloxyethane and 1,2-diacetoxyethane; halogenated hydrocarbons, such as dichloromethane, chloroform, carbon tetrachloride, dichloroethane, dibromoethane, and chlorobenzene; nitriles, such as acetonitrile and butyronitrile; and hydrocarbons, such as pentane, hexane, and cyclohexane. These solvents may be used alone or in combination. The solvent used for dissolving the chlorinated azetidinone derivative in solution A is hereinafter referred to as solvent A1.

The solvent A1 content is in the range of 50 to 500 parts by weight and preferably in the range of 100 to 500 parts by weight relative to 100 parts by weight of the chlorinated azetidinone derivative (Compound (4)).

The solution of the chlorinated azetidinone derivative may be used directly. However, it is preferable to add an alcohol to the solution from the viewpoint of reducing the viscosity to enhance the ease of a dripping operation. This alcohol is hereinafter referred to as solvent A2. Exemplary alcohols used as solvent A2 include lower alcohols, such as methanol, ethanol, 1-propanol, and 2-propanol. These alcohols may be used alone or in combination. Among these lower alcohols, methanol or ethanol is preferably used because a reaction under the conditions described later using methanol or ethanol can provide a highly pure crystalline 3-chloromethyl-3-cephem derivative expressed by Chemical Formula (6) with a high yield.

The alcohol (solvent A2) content is in the range of 100 to 500 parts by weight and preferably in the range of 200 to 300 parts by weight relative to 100 parts by weight of the chlorinated azetidinone derivative expressed by Chemical Formula (4).

Preferably, the chlorinated azetidinone derivative content in solution A is in the range of 0.05 to 1 mol/L and more preferably in the range of 0.1 to 0.5 mol/L.

Solution B:

In the present invention, an alcoholate is used in crystallization in the third step.

The alcoholate is expressed by Chemical Formula $R_4$-MO wherein $R_4$ represents a straight or branched lower alkyl group having a carbon number in the range of 1 to 4, such as methyl, ethyl, isopropyl, or n-propyl, and M represents an alkali metal atom, such as lithium, sodium, or potassium. Exemplary alcoholates include sodium methylate, sodium ethylate, potassium methylate, potassium ethylate, lithium methylate, lithium ethylate, and potassium t-butylate. These alcoholates may be used alone or in combination.

Among these alcoholates, sodium methylate or sodium ethylate is preferably used because a reaction under the conditions described later using sodium methylate or sodium ethylate can provide a highly pure crystalline 3-chloromethyl-3-cephem derivative expressed by Chemical Formula (6) with a high yield.

Solution B containing such an alcoholate is prepared using a solvent capable of dissolving the alcoholate so as to have a predetermined concentration.

The solvent capable of dissolving the alcoholate is preferably at least one of alcohols, such as methanol, ethanol, 1-propanol, and 2-propanol. This solvent is hereinafter referred to as solvent B1. Among these alcohols, methanol or ethanol is preferably used because a reaction under the conditions described later using methanol or ethanol can provide a highly pure crystalline 3-chloromethyl-3-cephem derivative expressed by Chemical Formula (6) with a high yield.

Solution C:

Solution C containing an alcohol includes a mixed solvent of at least an alcohol (hereinafter referred to as solvent C1) and another solvent (hereinafter referred to as solvent C2). Exemplary alcohols used as solvent C1 include lower alcohols, such as methanol, ethanol, 1-propanol, and 2-propanol. These alcohols may be used alone or in combination. Among these alcohols, methanol or ethanol is preferably used.

While alcohols dissolve the starting material, the chlorinated azetidinone derivative expressed by Chemical Formula (1), the alcohols do not dissolve the reaction product, the 3-chloromethyl-3-cephem derivative expressed by Chemical Formula (2). Therefore, the alcohols are suitable as a reaction solvent for directly recovering the reaction product in a crystal form.

Solvent C2, which is used in combination with solvent C1 being an alcohol (solvent C1), preferably dissolves the starting material, the chlorinated azetidinone derivative (Compound (4)), and also dissolves impurities after reaction, such as the unreacted starting material, the chlorinated azetidinone derivative, and reaction byproducts, thus helping recover a highly pure crystalline 3-chloromethyl-3-cephem derivative (Compound (6)) from the reaction solution. Exemplary solvents C2 include esters, such as methyl formate, ethyl formate, methyl acetate, ethyl acetate, butyl acetate, and ethyl propionate; halogenated hydrocarbons, such as dichloromethane, chloroform, carbon tetrachloride, dichloroethane, dibromoethane, and chlorobenzene; ethers, such as diethyl ether, diisopropyl ether, dibutyl ether, dioxane, and tetrahydrofuran; nitrites, such as acetonitrile and butyronitrile; and hydrocarbons, such as pentane, hexane, and cyclohexane. These solvents may be used alone or in combination. Among these solvents, ethers are preferably used as solvent C2.

The solvent C2 content in the mixed solvent with the alcohol (solvent C1) is in the range of 10 to 30 parts by weight and preferably in the range of 10 to 20 parts by weight relative to 100 parts by weight of solvent C1. By performing the reaction in such proportions under conditions described below, a highly pure crystalline 3-chloromethyl-3-cephem derivative expressed by Chemical Formula (6) can be prepared with a high yield. A solvent C2 content of less than 10 parts by weight causes the crystals of the 3-chloromethyl-3-cephem derivative to increasingly hold impurities, such as reaction byproducts, and aggregate as the reaction proceeds. Thus, it becomes difficult to provide a highly pure crystalline 3-chloromethyl-3-cephem derivative with a high yield. A solvent C2 content of more than 30 parts by weight causes the crystalline 3-chloromethyl-3-cephem derivative to dissolve, thus undesirably reducing the yield.

Solution C containing an alcohol is preferably used in an amount in the range of 300 to 2,000 parts by weight and more preferably in the range of 500 to 1,000 parts by weight relative to 100 parts by weight of the chlorinated azetidinone derivative expressed by Chemical Formula (4). An amount of less than 300 parts by weight of solvent C makes the progress of the reaction difficult, leaving unreacted materials. An amount of more than 2,000 parts by weight consumes an excessive amount of solvent, thus leading to an industrial disadvantage.

Reaction Conditions:

In the present invention, the third step is performed at a pH of 8 or less and preferably at a pH of 6 to 8 by adding dropwise solution A containing the chlorinated azetidinone derivative expressed by Chemical Formula (4) and solution B containing the alcoholate expressed by Chemical Formula (5) into solution C containing an alcohol.

At a pH of more than 8, the crystals of the 3-chloromethyl-3-cephem derivative are decomposed during the reaction and, consequently, a desired crystalline 3-chloromethyl-3-cephem derivative is not provided with a high yield. This is because the reaction product, the 3-chloromethyl-3-cephem derivative, is extremely unstable against alkalis.

Since the reaction proceeds rapidly, the pH is preferably measured with litmus paper or a pH meter. In use of the litmus paper, a drop is taken from the reaction system to the litmus paper and water is added to the drop. In use of the pH meter, a small amount of sample taken from the reaction system is diluted with water in an amount twice that of the sample, and the pH of the diluted sample is measured. The pH of the reaction system increases because unreacted part of the alcoholate is weakly basic, and accordingly the reaction system becomes alkaline during the reaction Therefore, the pH is preferably controlled in the above-described range during dripping of solution A containing the chlorinated azetidinone derivative and solution B containing the alcoholate into solution C containing an alcohol.

Solution A and solution B are added dropwise in such proportions that the molar amount of the alcoholate in solution B is in the range of 0.8 to 1.5 times and preferably in the range of 1.1 to 1.2 times that of the chlorinated azetidinone derivative (Compound (4)), from the viewpoint of reducing the amount of the unreacted part of the starting material, the chlorinated azetidinone derivative (Compound (4)). Thus, a highly pure crystalline 3-chloromethyl-3-cephem derivative can advantageously be obtained with a high yield. An amount of less than 0.8 time moles of alcoholate allows an excessive amount of the chlorinated azetidinone derivative to remain unreacted. An amount of more than 1.5 times moles makes the reaction solution alkali at a pH of more than 8, and consequently, the resulting crystalline 3-chloromethyl-3-cephem derivative is undesirably decomposed.

In addition, solution A and solution B are preferably added dropwise in such proportions that the total content of the alcohols (solvents A2, B1, and C1) in the total of the reaction solvents (solvents A1, A2, B1, C1, and C2) of all solutions A to C is in the range of 30 to 95 percent by weight and more preferably in the range of 60 to 90 percent by weight after completion of the addition. A total alcohol content of less than 30 percent by weight in the solvents after the addition makes it difficult to dissolve the alcoholate being a reactant in the reaction solution, and causes the crystalline 3-chloromethyl-3-cephem derivative to dissolve, consequently reducing the yield. A total alcohol content of more than 95 percent by weight causes the crystals of the resulting 3-chloromethyl-3-cephem derivative to increasingly hold the impurities, such as reaction byproducts, and aggregate as the reaction proceeds. Thus, it becomes difficult to provide a highly pure 3-chloromethyl-3-cephem derivative with a high yield.

Most preferably, solution A contains a mixed solvent containing an ether (solvent A1) and at lease one of methanol and ethanol (solvent A2) as a solvent for dissolving the chlorinated azetidinone derivative (Compound (4)); solution B contains at least one of methanol and ethanol (solvent B1); and solution C contains a mixed solvent of at least one of methanol and ethanol (solvent C1) and an ether (solvent C2). These solutions are added dropwise in such proportions that the total alcohol content in the total of solvents A1, A2, B1, C1, and C2 is in the range of 20 to 60 percent by weight and preferably in the range of 30 to 50 percent by weight after completion of the addition. Consequently, a highly pure crystalline 3-chloromethyl-3-cephem derivative expressed by Chemical Formula (6) can be advantageously provided with a high yield.

For dripping solution A and solution B into solution C, any one of the following two methods may be applied.

(1) Solution A and solution B are continuously or intermittently dripped into solution C in such a manner that solution A is added before solution B so as to control the pH of the reaction system in the above-described range.

(2) First, part of solution A is dripped into solution C so that the amount added is 5 to 30 mol percent and preferably 10 to 20 mol percent of the equivalent of the entire chlorinated azetidinone derivative involved in the reaction, and then, the rest of solution A is dripped into solution C together with solution B so as to control the pH of the reaction system in the above-described range.

In the former method (1), solutions A and B are dripped into solution C in an appropriate order so as to maintain the pH of the reaction system in the above-described range.

In the latter method (2), a predetermined amount of solution A is dripped into solution C in advance to make the reaction system acid (for example, pH 4), and then the rest of solution A and solution B are substantially simultaneously dripped into solution C in succession so as to maintain the pH of the reaction system in the above-described range.

In the third step, part of the chlorinated azetidinone derivative may be added to solution C in advance so that the amount added is 5 to 30 mol percent and preferably 10 to 30 mol percent of the reaction equivalent of the entire azetidinone derivative involved in the reaction. Then, necessary amounts of solution A and solution B may be simultaneously dripped into solution C so as to maintain the pH of the reaction system in the above-described range.

The reaction product, the 3-chloromethyl-3-cephem derivative obtained by the third step, is extremely unstable against alkalis, and is accordingly decomposed at a pH of 8 or more during the reaction. It is therefore preferable to drip solution A ahead of solution B to maintain the pH of the reaction system at 8 or less, as described in the foregoing two dripping methods, because if solutions A and B are simultaneously dripped into solution C from the start, the reaction system is likely to become alkaline. Solution A has a pH of about 4, and adding solution B increases the pH of the reaction system.

In the third step of the present invention, preferably, the latter method (2) is applied from the viewpoint of ease of pH control, that is, an industrial advantage.

The entire amount of solution A may be added to solution C, and then solution B may be dripped into solution C to perform the reaction at a pH of 8 or less. In this method, the crystals of the reaction product, the 3-chloromethyl-3-cephem derivative, are liable to hold impurities, and thus the quality is liable to be so degraded that a large amount of purification load is required in a subsequent step. However, the product can be provided in a crystal form in a single step and the reaction can be allowed to proceed through a simple operation.

Solution A containing the starting material, the chlorinated azetidinone derivative, may be a solution of the chlorinated azetidinone derivative resulting from the second step of chlorinating an azetidinone derivative to prepare the chlorinated azetidinone derivative. By using this solution, the targeted 3-chloromethyl-3-cephem derivative can be prepared from the azetidinone derivative used as the starting material in the second step through continuous steps.

In the third step of the present invention, in order to decrease the viscosity of solution A, methanol or ethanol may be added to dilute the solution so that the solution is easy to drip.

In the third step, the reaction proceeds in a nonaqueous solvent and does not produce water. Therefore, the alcoholate is not dissolved in water and does not act as an alkali. Thus, the process of the present invention advantageously helps prevent such an alkali from decomposing the reaction product, the crystalline 3-chloromethyl-3-cephem derivative.

Preferably, the reaction is performed at a temperature of 5° C. or less from the viewpoints of preventing byproducts and of producing the targeted crystalline 3-chloromethyl-3-cephem derivative expressed by Chemical Formula (6) with high purity. However, a temperature of less than −20° C. causes the raw materials or impurities to precipitate. Accordingly, the reaction is preferably performed at a temperature in the range of −20 to 5° C. and more preferably in the range of −10 to 5° C.

The reaction proceeds to successively precipitate the targeted 3-chloromethyl-3-cephem derivative expressed by Chemical Formula (6). After the completion of the reaction, the resulting solution is neutralized, and the precipitates are recovered from the reaction solution by solid-liquid separation and dried to yield the 3-chloromethyl-3-cephem derivative as a crystalline product. The recovered crystalline product may be purified by washing and recrystallization, if necessary. Solvents used for recrystallization include alcohols, such as methanol, ethanol, 1-propanol, and 2-propanol; nitrites, such as acetonitrile and butyronitrile; ketones, such as acetone and methyl ethyl ketone; and amides, such as dimethylformamide and diethylformamide. These solvents may be appropriately used alone or in combination.

Furthermore, the present invention provides a method further including the following steps:

Fourth step: collecting a metal sulfinate (Compound (7)) produced as a by-product in the third step from the mother liquid after the solid-liquid separation.

Fifth step: providing a sulfonyl halide (Compound (2)) by a reaction of the collected metal sulfinate (Compound (7)) with a halogen in a solvent.

The sulfonyl halide obtained by the fifth step can be recycled as a raw material of the above-described first step of the present invention.

Fourth Step:

The fourth step includes collecting the metal sulfinate from the recovered mother liquid after the third step.

The metal sulfinate (Compound (7)) content in the mother liquid after the third step is in the range of 0.05 to 0.5 mol/L and more preferably in the range of 0.05 to 0.2 mol/L. The mother liquid after the third step is subjected to neutralization of the unreacted alcoholate with an acetic acid or dilute hydrochloric acid and thus contains impurities such as neutral salts, for example, sodium acetate, sodium chloride, or the like. Therefore, the mother liquid contains an alcohol as a main component at a pH of 2 to 10 and preferably at a pH of 2 to 6.

The fourth step is a step in which first, the recovered mother liquid is concentrated. The concentration step can improve the recovery percentage of the metal sulfinate (compound (7)). In the concentration step, preferably, 50 to 90 percent by weight and preferably 80 to 85 percent by weight of the mother liquid is recovered, and the concentrated liquid contains the metal sulfinate (compound (7)) at 0.4 to 0.9 mol/L and preferably 0.6 to 0.8 mol/L. The concentrated mother liquid usually has a pH of 2 to 5 and preferably a pH of 3 to 4.

The next step is a step in which the concentrated mother liquid undergoes neutralization with an alkali. The concentrated mother liquid has a pH of 6 to 7 after the neutralization to give the metal sulfinate by neutralization of free sulfinic acid. Exemplary alkalis include sodium hydroxide, potassium hydroxide, sodium carbonate, potassium carbonate, and sodium hydrogencarbonate. The alkali is a generally used alkali and is not particular limited.

The next step is a step in which at least one organic solvent selected from toluene, xylene, benzene, ethyl acetate, dichloromethane, and 1,2-dichloroethane is added to the concentrated liquid after the neutralization, and the solvent is removed by distillation. The organic solvent content is in the range of 20 to 200 parts by weight and preferably in the range of 50 to 100 parts by weight relative to 100 parts by weight of the above-described concentrated liquid. Water is recovered by azeotropic distillation, and the organic solvent and residual alcohol are removed from the concentrated liquid to obtain a residue.

The next step is a step in which at least one solvent selected from acetone, methyl ethyl ketone, diethyl ketone, methyl isobutyl ketone, and diisobutyl ketone is added to the residue to precipitate the metal sulfinate (compound (7)) under cooling. The metal sulfinate (compound (7)) is then recovered by a solid-liquid separation.

The cooling temperature is less than 50° C. and preferably in the range of −10 to 20° C. Thus, the highly pure metal sulfinate (compound (7)) can be advantageously provided with a high yield.

The reaction proceeds to precipitate the metal sulfinate (compound (7)), and the precipitates are recovered by solid-liquid separation, and, if required, washed with water and dried to yield the metal sulfinate (compound(7)).

Fifth Step:

The fifth step includes a reaction of the metal sulfinate (compound (7)) obtained by the fourth step with a halogen (compound (8)) in a solvent to produce the sulfonyl halide (compound (2)) according to the following Reaction Formula (5):

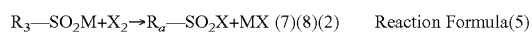

wherein $R_3$, M, and X defined as described above.

In this step, 0.8 to 1.1 and preferably 0.95 to 1.05 times moles of the halogen (Compound (8)) is added per mole of the metal sulfinate (compound (7)). This is due to the fact that when the amount of the halogen added is less than 0.8 time moles, large amounts of unreacted raw materials are left, and the reaction product, the sulfonyl halide, is provided with a low yield and low purity. On the other hand, when the amount is more than 1, 1 times moles, a lot of halogen remains, and thus halogenation of the solvent undesirably proceeds.

A mixed solvent of at least one organic solvent and water can be preferably used as the solvent in the fifth step. Exemplary organic solvents having slight solubility in water include hydrocarbons, such as toluene, benzene, xylene, hexane, and cyclohexane. In particular, a mixed solvent of toluene and water is preferably used because separation between the sulfonyl halide and salt can be easily performed after the reaction. With respect to the mixing ratio between the organic solvent and water, the water content is in the range of 20 to 200 parts by weight and preferably 50 to 100 parts by weight relative to 100 parts by weight of the organic solvent.

The reaction temperature should be set between 0 to 80° C. and preferably between 0 to 20° C., and the reaction time is between 0.5 to 10 hours and preferably between 2 to 6 hours.

After the reaction, if necessary, aging can be further performed for decreasing the amount of free halogen at 10 to 20° C. for 0.1 to 5 hours. Further, in the present invention, the metal sulfinate (compound (7)) may be added to the aged solution during the aging so that free halogen can decreased by reaction of the metal sulfinate with the unreacted free halogen.

After the aging, the aged solution is washed with a solution of sodium chloride or the like, and an organic layer is recovered and dried under reduced pressure, whereby the sulfonyl halide (compound (2)) is obtained.

The sulfonyl halide (compound (2)) obtained by the fourth and fifth steps can be recycled as a raw material in the first step, and the sulfonyl halide (compound (2)) can be used in the first step, whereby the highly pure crystalline 3-chloromethyl-3-cephem derivative (compound (6)) can be advantageously provided with a high yield through the first to third steps.

The crystalline 3-chloromethyl-3-cephem derivative expressed by Chemical Formula (6) produced by the process of the present invention is stable for a long time under moderate conditions, and can be converted into a 7-amino-3-chloromethyl-3-cephem derivative, which is useful for cephalosporin antibiotics.

EXAMPLES

The present invention will now be further described with reference to examples, but it is not limited to these examples.

Example 1

<First step>

An azetidinone derivative (Compound (11)) was prepared from a thiazoline azetidinone derivative (Compound (9)) according to the following Reaction Formula (6):

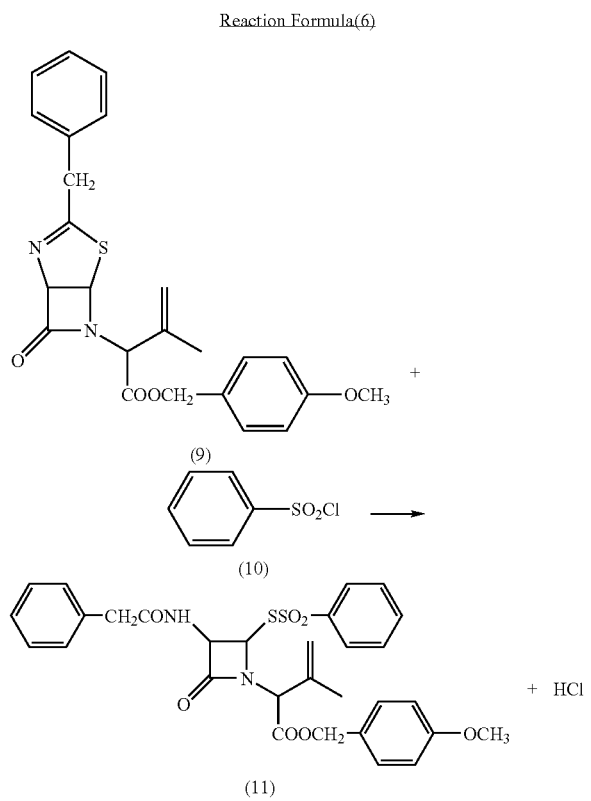

A reaction flask was charged with 323.8 g of a toluene solution containing 28.3 percent of the thiazoline azetidinone derivative (compound (9)), and 200 mL of n-propanol was charged into the flask. Next, 30 mL of 1N-hydrochloric acid was added into the flask at 25° C. or less, and 63.6 g (1.2 times moles) of a toluene solution containing 70 percent of a benzene sulfonyl chloride (compound (10)) was added to the resultant mixture, followed by stirring at 25° C. for 8 hours.

After reaction, 100 mL of toluene and 180 mL of ion-exchange water were charged in the reaction solution. An organic layer was separated, and washed and dried by conventional means to give 113.3 g of white crystals of the azetidinone derivative (compound (11)). The measured product purity was 94.5% as compared with a separately purified standard. The product yield was 85.7%.

Identification Data:
$^1$H-NMR (δ, CDCl$_3$) 5.81 (1H, d, j=4.8), 5.07 (1H, d, d, j=7.7, 4.8), 6.42 (1H, d, j=7.7), 3.58 (1H, d, j=16.2), 3.52 (1H, d, j=16.2), 7.22-7.35 (5H, m), 4.76 (1H, s), 4.73 (1H, s), 4.41 (1H, s), 1.73 (3H, s), 5.10 (1H, d, j=12.1), 5.03 (1H, d, j=12.1), 7.26 (2H, d, j=8.6), 6.88 (2H, d, j=8.6), 3.83 (3H, s), 7.47 (2H, j=8.0), 7.80 (2H, t, j=8.0), 7.59 (1H, d, j=8.0)

FT-IR (cm$^{-1}$, KBr)
3488 cm$^{-1}$, 1778 cm$^{-1}$, 1736 cm$^{-1}$, 1645 cm$^{-1}$, 1250 cm$^{-1}$, 1145 cm$^{-1}$

FAB-MS M+1:595 m/z

<Second Step>

A chlorinated azetidinone derivative (Compound 12)) was prepared from the azetidinone derivative (Compound (11)) obtained by the first step according to following Reaction Formula (7):

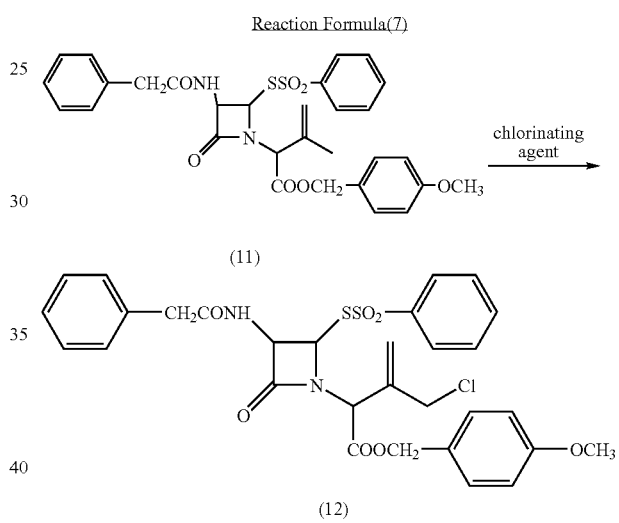

A reaction flask in which air was replaced with nitrogen was charged with 196.3 g (0.33 mole; amount corrected for purity, 0.3119 mole) of the azetidinone derivative (compound (11)) obtained by the first step, and the azetidinone derivative was dissolved in 4040 g of tetrahydrofuran. Next, 54.1 g of calcium oxide (1.0 mole) was charged, and chlorine was blown into the flask at a temperature of 25 to 30° C. In this operation, 29.4 g (0.415 mole) of the chlorine was blown for about 10 hours. The reaction was performed to an end point where the peak area ratio of the raw material, the azetidinone derivative (compound (11)), to the peak area of the chlorinated azetidinone (compound (12)) was less than 1%.

Then, the tetrahydrofuran was recovered using a rotary evaporator at a temperature of 25 C or less. The weight of the concentrated solution was controlled to 364 g. Liquid chromatographic (LC) quantitative analysis revealed that the resulting tetrahydrofran solution contained 46.9% (weight: 170.72 g; 0.271 mole equivalent, the yield: 87.0%) of the chlorinated azetidinone derivative (compound (13)) based on a separately purified standard sample.

Identification Data:
$^1$H-NMR(δ, CDCl$_3$) 5.86 (1H, d, j=4.8), 5.00 (1H, d, D, j=4.8, 7.5), 6.05 (1H, d, j=7.5), 3.56 (1H, d, j=16.3), 3.62 (1H, d, j=16.3), 7.22-7.35 (5H, m), 5.12 (1H, s), 4.60 (1H, s), 5.12 (1H, s), 4.00 (1H, d, j=12.1), 4.17 (1H, d, j=12.1), 5.07 (1H, d, j=11.8), 5.14 (1H, d, j=11.8), 7.28 (2H, d, j=8.8), 6.90 (2H, d, j=8.8), 3.82 (3H, s), 7.48 (2H, j=7.9), 7.80 (2H, t, j=7.9), 7.60 (1H, d, j=7.9)

FT-IR ($cm^{-1}$, KBr)
3359 $cm^{-1}$, 1781 $cm^{-1}$, 1739 $cm^{-1}$, 1670 $cm^{-1}$, 1247 $cm^{-1}$, 1143 $cm^{-1}$

FAB-MS
M+1:629 m/z

<Third Step>

A 3-chloromethyl-3-cephem derivative (compound (13)) was prepared from the tetrahydrofuran solution containing the azetidinone derivative (Compound (12)) obtained by the second step according to following Reaction Formula (8):

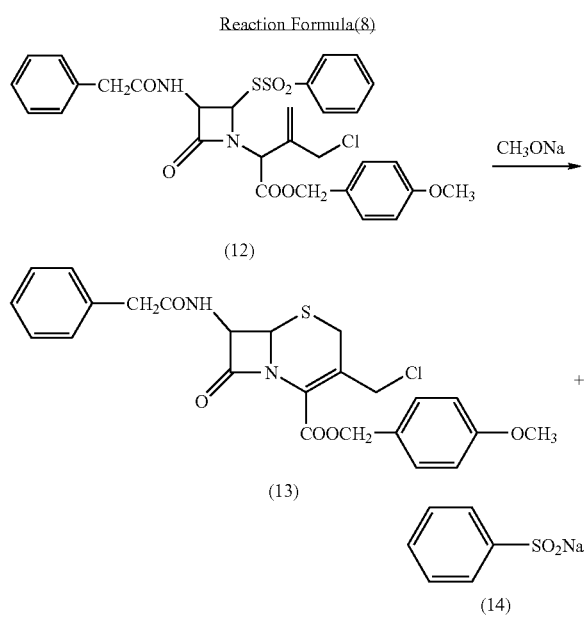

A dropping funnel in which air was replaced with nitrogen was charged with 323.3 (0.241 mole) of the tetrahydrofuran solution containing 46.9 percent by weight of the chlorinated azetidinone derivative (compound (12)) synthesized in the second step. The tetrahydrofuran solution was diluted with 232 g of dehydrated methanol (produced by Kanto Kagaku) to prepare solution A.

On the other hand, 53.7 g of a solution containing 28 percent by weight of sodium methylate in extra-pure methanol was diluted with 311.5 g of dehydrated methanol to prepare solution B containing 4 percent by weight of the sodium methylate in methanol.

A four-neck reaction flask was charged with 60 g of tetrahydrofuran and 740 mL of dehydrated ethanol, followed by cooling to −2 to 2° C. One-eighth of the entire amount of solution A was placed in the flask containing the cooled reaction solvents. The resulting solution had a pH of 4. While the temperature of the reaction system was maintained in the range of −2 to 2° C., solution A and solution B were simultaneously dripped. Upon dripping about one-eighth of solution B, the reaction liquid started to become clouded and formed a slurry containing white crystals. Furthermore, solution A and solution B were simultaneously dripped so that the whole of the solutions is completely dripped over a period of about 5 hours. The resulting reaction solution had a pH in the range of 7 to 8. After the completion of dripping, the reaction was continued at 0° C. for another 0.25 hour with stirring.

After the completion of the reaction, 2.3 g of acetic acid was added to neutralize the resulting reaction solution. The reaction solution had a pH in the range of 4 to 5 after the neutralization. Then, the reaction solution was stirred at −2 to 2° C. for 0.5 hour for ageing. After ageing, the reaction solution was filtered through a G3 glass filter. The resulting cake was washed and dried by conventional means. Thus, 104.7 g of a 3-chloromethyl-3-cephem derivative (compound (13)) was yielded (purity: 94.8%, yield: 84.6%).

On the other hand, 1345.5 g of a filtered mother liquid containing sodium benzenesulfinate dihydrate was yielded; hence, the mother liquid contained 0.241 mol of sodium benzenesulfinate.

Identification Data:
$^1$H-NMR(δ, $CDCl_3$) 3.41 (1H, d, j=18.5), 3.59 (1H, D, J=18.5), 4.92 (1H, D, J=4.9), 5.82 (1H, D, D, j=4.9,9.3), 6.12 (1H, d, j=9.3), 3.58 (1H, d, j=16.1), 3.67 (1h, d, j−16.1), 7.40-7.28 (5H, m), 4.39 (1H, d, j=11.9), 4.50 (1H, d, j=11.9), 5.20 (2H, s), 7.32 (2H, d, j=8.6), 6.88 (2H, d, j=8.6), 3.80 (3H, s)

FT-IR ($cm^{-1}$, KBr)
3449 $cm^{-1}$, 3271 $cm^{-1}$, 1778 $cm^{-1}$, 1703 $cm^{-1}$, 1645 $cm^{-1}$, 1251 $cm^{-1}$

FAB-MS M+1:487 m/z

The resulting crystalline 3-chloromethyl-3-cephem derivative obtained in Example 1 was subjected to X-ray diffraction analysis with an X-ray diffractometer RINT 2400 produced by Rigaku, using copper radiation at a wavelength of 1.5418 Å passed through a monochrometer filter. The results obtained from the X-ray diffraction pattern are shown in Table 1.

TABLE 1

| d | $I/I_0$ |
|---|---|
| 12.91 | 0.81 |
| 11.67 | 0.64 |
| 6.45 | 0.39 |
| 6.32 | 0.29 |
| 5.80 | 0.48 |
| 4.94 | 0.31 |
| 4.72 | 0.65 |
| 4.65 | 0.89 |
| 4.50 | 0.71 |
| 4.44 | 0.33 |
| 4.28 | 0.58 |
| 4.16 | 1.00 |
| 4.04 | 0.13 |
| 3.97 | 0.15 |
| 3.85 | 0.71 |
| 3.77 | 0.50 |
| 3.70 | 0.11 |
| 3.45 | 0.46 |
| 3.37 | 0.20 |
| 3.20 | 0.13 |
| 3.16 | 0.18 |
| 3.09 | 0.12 |
| 2.90 | 0.13 |

In Table 1, d represents lattice spacing; and $I/I_0$, relative intensity to a diffraction peak at d=4.17.

The filtered mother liquid obtained by the third step was used in the following step.

<Fourth Step>

First, 1300.0 g of the filtered mother liquid, containing 0.233 mole of the chlorinated azetidinone derivative (compound (13)), obtained by the third step was concentrated until 309.4 g of the filtered mother liquid was obtained. The rate of concentration was 76.2%.

The concentrated solution was mixed with 240 mL of toluene. Then, 11.3 of 50% sodium hydroxide was added to neutralize the resulting mixture. As a result, the mixture was neutralized from pH 5 to pH 7. Then the mixture was concentrated to 203.5 g at 45° C. and 30 mmHg.

Next, the sodium benzenesulfinate was precipitated by adding 140 mL of acetone cooled to 0° C. The sodium benzenesulfinate was filtrated off through a G3 glass filter and washed with 170 mL of cooled acetone three times. The glass filter with the sodium benzenesulfinate was dried in a desiccator at room temperature in a vacuum of 10 mmHg. Thus, 31.66 g of a white crystalline sodium benzenesulfinate was yielded. Liquid chromatographic (LC) analysis revealed that the purity was 95.8% as compared with a standard sample having a rough yield of 67.9%, and the true yield was 65.0% (0.151 mole) based on the chlorinated azetidinone derivative (compound (13)).

Identification Data:
$^1$H-NMR (D$_2$O) 7.53-7.66 (5H, m)
FAB-MS (NEG) M−23:141 m/z <Fifth Step>

A reactor was charged with 29.3 g of sodium benzenesulfinate (0.14 mole) obtained by the fourth step, and the benzenesulfinate was dissolved in 65 mL of water. Then, 105 mL of toluene was charged, and 10.3 g (0.1456 mole, 1.04 times moles) of chlorine was, little by little, blown into the reactor at a temperature of 18 to 20° C. The reaction solution was aged at the same temperature of 18 to 20° C. with stirring, and separated into an organic layer and an aqueous layer. The organic layer was washed with 90 g of a 3% aqueous sodium chloride solution and then concentrated at a reduced pressure and 45° C. or less to obtain 32.9 g of a benzenesulfonyl chloride solution. Gas chromatographic quantitative analysis revealed that the concentration of benzenesulfonyl chloride in the organic layer was 70.7% (weight; 24.21 g, 0.1371 mole), and the yield was 93.9%

Identification Data:
EI-MS M+:176 m/z

Example 2

The first step to third step were performed to effect reaction using the benzene sulfonyl chloride obtained by the fifth step of Example 1.

First Step

A reaction flask was charged with 143.2 g of a toluene solution containing 28.3 percent of the thiazoline azetidinone derivative (compound (9)), and 122 mL of n-propanol was charged into the flask. Then, 14 mL of 1N hydrochloric acid was added at 20° C. or less, and 27.87 g (1.2 times moles) of a toluene solution containing 70.7 percent of the benzenesulfonyl chloride (compound (10; X=Cl)) collected in the above-described fifth step was dripped into the flask, followed by stirring at 25° C. for 8 hours.

After reaction, 45 mL of toluene and 80 mL of ion exchange water were charged in the reaction solution. An organic layer was separated, and washed and dried by conventional means to give 48.9 g of a white crystalline azetidinone derivative (compound (11)). The measured product purity was 95.9% as compared with a separately purified standard sample. The product yield was 84.9%.

Identification Data:
$^1$H-NMR (δ, CDCl$_3$) 5.81 (1H, d, j=4.8), 5.07 (1H, d, d, j=7.7, 4.8), 6.42 (1H, d, j=7.7), 3.58 (1H, d, j=16.2), 3.52 (1H, d, j=16.2), 7.22-7.35 (5H, m), 4.76 (1H, s), 4.73 (1H, s), 4.41 (1H, s), 1.73 (3H, s), 5.10 (1H, d, j=12.1), 5.03 (1H, d, j=12.1), 7.26 (2H, d, j=8.6), 6.88 (2H, d, j=8.6), 3.83 (3H, s), 7.47 (2H, j−8.0), 7.80 (2H, t, j−8.0), 7.59 (1H, d, j=8.0)
FT-IR (cm$^{-1}$, KBr) 3448 cm cm
−1, 1778 cm$^{-1}$, 1736 cm$^{-1}$, 1645 cm$^{-1}$, 1250 cm$^{-1}$, 1145 cm$^{-1}$
FAB-MS M+1:595 m/z <Second Step>

A reaction flask in which air was replaced with nitrogen was charged with 45.27 g (0.073 mole) of the azetidinone derivative (compound (11)) obtained by the first step, and the derivative was dissolved in 945 g of tetrahydrofuran. Next, 12.7 g of calcium oxide (0.23 mole) was charged, and chlorine was blown into the flask at a temperature of 25 to 30° C. The reaction was carried out while checking the progress of the reaction for finding the end point of chlorine blowing by high performance liquid chromatography (LC). During the reaction, 6.30 g (0.089 mole) of chlorine was blown into the flask for about 5 hours.

Next, the tetrahydrofuran was recovered using a rotary evaporator at a temperature of 25° C. or less. The weight of the concentrated solution was controlled to 82 g. Liquid chromatographic (LC) quantitative analysis revealed that the resulting tetrahydrofuran solution contained 48.4 percent (39.69 g, 0.0631 mole equivalent) of the chlorinated azetidinone derivative (MW: 629.14) (compound (12) based on a separately purified standard sample. The product yield was 86.4%.

Identification Data:
$^1$H-NMR(δ, CDCl$_3$) 5.86 (1H, d, j=4.8), 5.00 (1H, d, d, j=4.8, 7.5), 6.05 (1H, d, j=7.5), 3.56 (1H, d, j=16.3), 3.62 (1H, d, j=16.3), 7.22-7.35 (5H, m), 5.12 (1H, s), 4.60 (1H, s), 5.12 (1H, s), 4.00 (1H, d, j=12.1), 4.17 (1H, d, j=12.1), 5.07 (1H, d, j=11.8), 5.14 (1H, d, j=11.8), 7.28 (2H, d, j=8.8), 6.90 (2H, d, j=8.8), 3.82 (3H, s), 7.48 (2H, j=7.9), 7.80 (2H, t, j=7.9), 7.60 (1H, d, j=7.9)
FT-IR (cm$^{-1}$, KBR)
3359 cm$^{-1}$, 1781 cm$^{-1}$, 1739 cm$^{-1}$, 1670 cm$^{-1}$, 1247 cm$^{-1}$, 1143 cm$^{-1}$
FAB-MS M+1:629 m/z <Third Step>

A dropping funnel in which air was replaced with nitrogen was charged with 67.59 g of a tetrahydrofuran solution containing 48.4 percent of the chlorinated azetidinone derivative (compound(12)) synthesized in the second step. The tetrahydrofuran solution was diluted with 50 g of dehydrated methanol (produced by Kanto Kagaku) to prepare solution A; hence, solution A contained 0.052 mole of the chlorinated azetidinone derivative.

On the other hand, 11.5 g of a solution containing 28 percent by weight of sodium methylate in extra pure methanol was diluted with 67.2 g of dehydrated methanol to prepare solution B containing 4 percent by weight of the sodium methylate in methanol.

A four-neck reaction flask was charged with 13 g of tetrahydrofuran and 160 mL of dehydrated ethanol, followed by cooling to −2 to 2° C. One-eighth of the entire amount of solution A was placed in the flask containing the cooled solvents. The resulting solution had a pH of 4. While the temperature of the reaction system was maintained in the range of −2 to 2° C., solution A and solution B were simultaneously dripped. Upon dripping about one-eighth of solution B, the reaction liquid started to become clouded and formed a slurry containing white crystals. Furthermore, solution A and solution B were simultaneously dripped so that the whole of the solutions was completely dripped over a period of about 4 hours. The resulting reaction solution had a pH in the range of 7 to 8. After the completion of dripping, the reaction was continued at 0° C. for another 0.25 hour with stirring.

After the completion of the reaction, 0.46 g of acetic acid was added to neutralize the resulting reaction solution. The reaction system had a pH in the range of 4 to 5 after the neutralization. Then, the reaction solution was aged at −2 to 2° C. for 0.5 hour under stirring. After ageing, the reaction solution was filtered through a G3 glass filter. The resulting cake was washed and dried by conventional means. Thus, 22.5 g of a crystalline 3-chloromethyl-3-cephem derivative (compound (13)) was yielded (purity: 94.8%, yield: 84.6%).

Identification Data:

$^1$H-NMR($\delta$, CDCl$_3$) 3.41 (1H, d, j=18.5), 3.59 (1H, d, j=18.5), 4.92 (1H, d, j=4.9), 5.82 (1H, d, d, j=4.9, 9.3), 6.12 (1H, d, j=9.3), 3.58 (1H, d, j=16.1), 3.67 (1H, d, j=16.1), 7.40-7.28 (5H, m), 4.39 (1H, d, j=11.9), 4.50 (1H, d, j=11.9), 5.20 (2H, s), 7.32 (2H, d, j=8.6), 6.88 (2H, d, j=8.6), 3.80 (3H, s)

FT-IR (cm$^{-1}$, KBr)

3449 cm$^{-1}$, 3271 cm$^{-1}$, 1778 cm$^{-1}$, 1703 cm$^{-1}$, 1645 cm$^{-1}$, 1251 cm$^{-1}$

FAB-MS M+1:487 m/z

The crystalline 3-chloromethyl-3-cephem derivative obtained in Example 2 was subjected to X-ray diffraction analysis with an X-ray diffractometer RINT 2400 produced by Rigaku, using copper radiation at a wavelength of 1.5418 Å passed through a monochromater filter. The results obtained from the X-ray diffraction pattern are shown in Table 2.

TABLE 2

| D | I/I$_0$ |
|---|---|
| 12.91 | 0.81 |
| 11.67 | 0.64 |
| 6.45 | 0.39 |
| 6.32 | 0.29 |
| 5.80 | 0.48 |
| 4.94 | 0.31 |
| 4.72 | 0.65 |
| 4.65 | 0.89 |
| 4.50 | 0.71 |
| 4.44 | 0.33 |
| 4.28 | 0.58 |
| 4.16 | 1.00 |
| 4.04 | 0.13 |
| 3.97 | 0.15 |
| 3.85 | 0.71 |
| 3.77 | 0.50 |
| 3.70 | 0.11 |
| 3.45 | 0.46 |
| 3.37 | 0.20 |
| 3.20 | 0.13 |
| 3.16 | 0.18 |
| 3.09 | 0.12 |
| 2.90 | 0.13 |

In Table 2, d represents lattice spacing; and I/I$_0$, relative intensity to a diffraction peak at d=4.16.

Example 3

<First Step, Second Step, and Third Step>

A crystalline 3-chloromethyl-3-cephem derivative was synthesized by procedures similar to those of Example 1 except that dioxane was used instead of tetrahydrofuran in the second step. Thus, 103.6 g of the crystalline 3-chloromethyl-3-cephem derivative (compound (13)) was yielded (purity: 94.6%, yield: 83.5%).

On the other hand, 1347.0 g of a filtered mother liquid containing sodium benzenesulfinate was yielded; hence, the mother liquid contained 0.241 mol of sodium benzenesulfinate.

<Fourth Step and Fifth Step>

Benzenesulfonyl chloride was synthesized with 1302.3 g of the mother liquid containing sodium benzenesulfinate by procedures similar to those of the fourth step and the fifth step of Example 1. Thus, 34.8 g of benzenesulfonyl chloride was yielded. Gas chromatographic quantitative analysis revealed that the concentration of benzenesulfonyl chloride in the organic layer was 68.8% (weight; 33.4 g, 0.1301 mole), and the yield was 92.8%.

Example 4

<First Step, Second Step, and Third Step>

A crystalline 3-chloromethyl-3-cephem derivative (Compound (13)) was synthesized by procedures similar those of the first step to the third step of Example 2 using the benzenesulfonyl chloride obtained by the fifth step in Example 3. Thus, 22.58 g of the crystalline 3-chloromethyl-3-cephem derivative (compound (13)) was yielded (purity: 94.4%, yield: 84.2%).

Example 5

<First Step, Second Step, and Third Step>

A crystalline 3-chloromethyl-3-cephem derivative (Compound (13)) was synthesized by procedures similar those of the first step to the third step of Example 1 except that benzenesulfonyl bromide was used instead of benzenesulfonyl chloride in the first step. Thus, 104.7 g of the crystalline 3-chloromethyl-3-cephem derivative (compound (13)) was yielded (purity: 94.7%, yield: 84.5%).

On the other hand, 1361.2 g of a filtered mother liquid containing sodium benzenesulfinate was yielded; hence, the mother liquid contained 0.241 mole of sodium benzenesulfinate.

<Fourth Step and Fifth Step>

Benzenesulfonyl bromide was synthesized with 1316.0 g of the mother liquid containing sodium benzenesulfinate by procedures similar to those of the fourth step and the fifth step of Example 1 except that bromine was used instead of chlorine in the fifth step. Thus, 36.0 g of benzenesulfonyl bromide was yielded. Gas chromatographic analysis revealed that the concentration of benzenesulfonyl bromide in the organic layer was 81.3% (weight; 29.27 g, 0.133 mole), and the yield was 94.4%.

Identification Data:

$^1$H-NMR (CDCl$_3$) 7.59-8.02 (5H, m)

FT-IR (KBr) 3067 cm$^{-1}$, 1579 cm$^{-1}$, 1365 cm$^{-1}$, 1168 cm$^{-1}$, 566 cm$^{-1}$

EI-MS M+:220 m/z

Example 6

<First Step, Second Step, and Third Step>

A crystalline 3-chloromethyl-3-cephem derivative (compound (13)) was synthesized by procedures similar to those of the first step to the third step of Example 4 using the benzenesulfonyl bromide obtained by the fifth step in Example 5. Thus, 22.82 g of the crystalline 3-chloromethyl-3-cephem derivative (Compound (13)) was yielded (purity: 94.0%, yield: 84.6%).

Example 7

<First Step, Second Step, and Third Step>

A crystalline 3-chloromethyl-3-cephem derivative was synthesized by procedures similar to those of Example 1 except that isopropyl ether was used instead of tetrahydrofuran, and propylene oxide was used instead of calcium oxide in the second step. Thus, 104.0 g of the crystalline 3-chloromethyl-3-cephem derivative (compound (13)) was yielded (purity: 94.6%, yield: 83.8%).

On the other hand, 1365.8 g of a filtered mother liquid containing sodium benzenesulfinate was yielded; hence, the mother liquid contained 0.241 mole of sodium benzene sulfinate.

<Fourth Step and Fifth Step>

Benzenesulfonyl bromide was synthesized with 1320.5 g of the mother liquid containing sodium benzene sulfinate by procedures similar to those of the fourth step and the fifth step of Example 5. Thus, 39.3 g of benzenesulfonyl bromide was yielded. Gas chromatographic quantitative analysis revealed that the concentration of benzenesulfonyl bromide in the organic layer was 73.7% (weight; 28.96 g, 0.131 mole), and the yield was 93.4%.

Example 8

<First Step, Second Step, and Third Step>

A crystalline 3-chloromethyl-3-cephem derivative (compound (13)) was synthesized by procedures similar to those of the first step to the third step of Example 6 using the benzene sulfonyl bromide obtained by the fifth step in Example 7. Thus, 22.62 g of the crystalline 3-chloromethyl-3-cephem derivative (compound (13)) was yielded (purity: 94.0%, yield: 84.0%).

Comparative Example 1

First, 71.48 g (0.104 mole) of a chlorinated azetidinone derivative was dissolved in 640 ml of dried dimethylformamide under nitrogen, followed by cooling to −30° C.; the chlorinated azetidinone derivative was synthesized by procedures similar to those of the first step and the second step of Example 1. While the temperature of the reaction system was maintained in the range of −30 to −20° C., 17.76 g (0.292 mole, 2.8 times moles) of aqueous ammonia was dripped little by little into the reaction solution. After dripping, the reaction solution was aged at −30 to −20° C. for 1.0 hour.

After ageing, 5% hydrochloric acid was added to the reaction solution to adjust the pH in the range of 4 to 5. Then, 1.92 L of ethyl acetate was charged into the reaction solution. An organic layer was separated at 0° C. and washed with a saturated sodium chloride solution two times. Furthermore, anhydrous sodium sulfate was added into the organic layer for dehydrating the organic layer.

The organic layer after dehydration was concentrated under reduced pressure to yield 38.0 g of an oily 3-chloromethyl-3-cephem derivative (compound (13)) (purity: 93.3.0%, yield: 70.7%).

Identification Data:

$^1$H-NMR($\delta$, CDCl$_3$) 3.41 (1H, d, j=18.5), 3.59 (1H, d, j=18.5), 4.92 (1H, d, j=4.9), 5.82 (1H, d, d, j=4.9, 9.3), 6.12 (1H, d, j=9.3), 3.58 (1H, d, j=16.1), 3.67 (1H, d, j=16.1), 7.40-7.28 (5H, m), 4.39 (1H, d, j=11.9), 4.50 (1H, d, j=11.9), 5.20 (2H, s), 7.32 (2H, d, j=8.6), 6.88 (2H, d, j=8.6), 3.80 (3H, s)

FT-IR (cm$^{-1}$, KBr)

3449 cm$^{-1}$, 3271 cm$^{-1}$, 1778 cm$^{-1}$, 1703 cm$^{-1}$, 1645 cm$^{-1}$, 1251 cm$^{-1}$

FAB-MS M+1:487 m/z

Stability Test:

The 3-chloromethyl-3-cephem derivatives prepared in Examples 1 to 8 and Comparative Examples 1 in an amount of 5 g were each placed in a sealed beaker and allowed to stand in a thermostatic chamber at 25° C. for 30 days.

Then, the purity of each sample of the 3-chloromethyl-3-cephem derivatives was measured. The results are shown in Table 3.

TABLE 3

|  | Purity before stability test (%) | Purity after 30 days (%) |
|---|---|---|
| Example 1 | 94.8 | 94.8 |
| Example 2 | 94.6 | 94.6 |
| Example 3 | 94.6 | 94.6 |
| Example 4 | 94.4 | 94.4 |
| Example 5 | 94.7 | 94.6 |
| Example 6 | 94.0 | 94.0 |
| Example 7 | 94.6 | 94.5 |
| Example 8 | 94.0 | 94.0 |
| Comparative example 1 | 93.3 | 89.9 |

According to the results of Table 3, the process of the present invention provides a crystalline 3-chloromethyl-3-cephem derivative that is stable for a long time under moderate conditions.

What is claimed is:

1. A process for preparing a 3-chloromethyl-3-cephem derivative comprising the following first to third steps:

First step: reacting a thiazoline azetidinone derivative with a sulfonyl halide in a solvent and in the presence of an acid to produce an azetidinone derivative, the thiazoline azetidinone derivative being expressed by Chemical Formula (1):

(1)

wherein R$_1$ and R$_2$ each represent an aromatic hydrocarbon group, sulfonyl halide being expressed by Chemical Formula (2):

$$R_3-SO_2X \quad (2)$$

wherein R₃ represents one selected form the group consisting of substituted or unsubstituted aryl groups and substituted or unsubstituted heterocyclic residues, and X represents a halogen atom, and the azetidinone derivative being expressed by Chemical Formula (3):

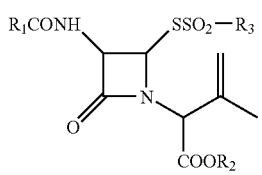
(3)

wherein R₁, R₂ and R₃ are the same as described above;
Second Step: reacting the azetidinone derivative obtained by the first step with a chlorination agent in an organic solvent to produce a chlorinated azetidinone derivative, the chlorinated azetidinone derivative being expressed by Chemical Formula (4):

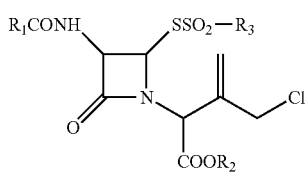
(4)

wherein R₁, R₂ and R₃ are the same as described above; and
Third Step: reacting the chlorinated azetidinone derivative obtained by the second step with an alcoholate in a solvent containing an alcohol and an ether at a pH of 8 or less to produce a 3-chloromethyl-3-cephem derivative in a crystal form, the alcoholate being expressed by Chemical Formula (5):

 (5)

wherein R₄ is an organic group and M is an alkali metal atom, and the 3-chloromethyl-3-cephem derivative being expressed by Chemical Formula (6):

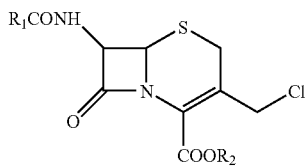
(6)

wherein R₁, R₂ and R₃ are the same as described above.

2. The process according to claim 1, wherein the third step includes adding solution A containing the chlorinated azetidinone derivative and solution B containing an alcoholate into solution C containing an alcohol, and wherein solution A is prepared by dissolving the chlorinated azetidinone derivative in a solvent containing an ether, and solution B is prepared by dissolving the alcoholate in a solvent containing an alcohol.

3. The process according to claim 1, wherein the reaction solution obtained by the third step is subjected to solid-liquid separation to separate a mother liquid containing the produced metal sulfinate and recover the precipitated 3-chloromethyl-3-cephem derivative in a crystal form.

4. A process for preparing a 3-chloromethyl-3-cephem derivative comprising the fourth and fifth steps below of preparing a sulfonyl halide from a metal sulfinate produced in the third step after a 3-chloromethyl-3-cephem derivative in a crystal form is recovered by the first to third steps of the process according to claim 1, wherein the sulfonyl halide obtained by the fourth and fifth steps can be used as a reaction raw material of the first step to perform the first to third steps:

Fourth step: recovering the metal sulfinate from a mother liquid of the reaction solution obtained by the third step, the metal sulfinate being expressed by Chemical Formula (7):

 (7)

wherein R₃ and M are the same as described above; and
Fifth step: reacting the metal sulfinate recovered by the fourth step 4 with a halogen in an organic solvent to produce a sulfonyl halide, the sulfonyl halide being expressed by Chemical Formula (2);

 (2)

wherein R₃ is the same as described above.

5. The process according to claim 4, wherein the fourth step comprises a step of concentrating the collected mother liquid after the third step 3, a step of neutralizing the concentrated solution to a pH of 6 to 7, a step of adding at least one organic solvent selected from toluene, xylene, benzene, ethyl acetate, dichloromethane and 1, 2-dichloroethane to the concentrated solution after the neutralization and then removing the organic solvent by distillation, and a step of adding at least one solvent selected from acetone, methyl ethyl ketone, diethyl ketone, methyl isobutyl ketone, and diisobutyl ketone to the residue after the organic solvent is removed by distillation, and then precipitating the metal sulfinate under cooling.

6. A process for preparing a 3-chloromethyl-3-cephem derivative comprising the fourth and fifth steps below of preparing a sulfonyl halide from a metal sulfinate produced in the third step after a 3-chloromethyl-3-cephem derivative in a crystal form is recovered by the first to third steps of the process according to claim 2, wherein the sulfonyl halide obtained by the fourth and fifth steps can be used as a reaction raw material of the first step to perform the first to third steps:

Fourth step: recovering the metal sulfinate from a mother liquid of the reaction solution obtained by the third step, the metal sulfinate being expressed by Chemical Formula (7):

 (7)

wherein R₃ and M are the same as described above; and
Fifth step: reacting the metal sulfinate recovered by the fourth step 4 with a halogen in an organic solvent to produce a sulfonyl halide, the sulfonyl halide being expressed by Chemical Formula (2);

 (2)

wherein R₃ is the same as described above.

7. The process according to claim 6, wherein the fourth step comprises a step of concentrating the collected mother liquid after the third step 3, a step of neutralizing the concentrated solution to a pH of 6 to 7, a step of adding at least one organic solvent selected from toluene, xylene, benzene, ethyl acetate, dichloromethane and 1, 2-dichloroethane to the concentrated solution after the neutralization and then removing the organic solvent by distillation, and a step of adding at least one solvent selected from acetone, methyl ethyl ketone, diethyl ketone, methyl isobutyl ketone, and diisobutyl ketone to the residue after the organic solvent is removed by distillation, and then precipitating the metal sulfinate under cooling.

8. A process for preparing a 3-chloromethyl-3-cephem derivative comprising the fourth and fifth steps below of preparing a sulfonyl halide from a metal sulfinate produced in the third step after a 3chloromethyl-3-cephem derivative in a crystal form is recovered by the first to third steps of the process according to claim 3, wherein the sulfonyl halide obtained by the fourth and fifth steps can be used as a reaction raw material of the first step to perform the first to third steps:

Fourth step: recovering the metal sulfinate from a mother liquid of the reaction solution obtained by the third step, the metal sulfinate being expressed by Chemical Formula (7):

R₃—SO₂M (7)

wherein R₃ and M are the same as described above; and

Fifth step: reacting the metal sulfinate recovered by the fourth step 4 with a halogen in an organic solvent to produce a sulfonyl halide, the sulfonyl halide being expressed by Chemical Formula (2);

R₃—SO₂X (2)

wherein R₃ is the same as described above.

9. The process according to claim 8, wherein the fourth step comprises a step of concentrating the collected mother liquid after the third step 3, a step of neutralizing the concentrated solution to a pH of 6 to 7, a step of adding at least one organic solvent selected from toluene, xylene, benzene, ethyl acetate, dichloromethane and 1, 2-dichloroethane to the concentrated solution after the neutralization and then removing the organic solvent by distillation, and a step of adding at least one solvent selected from acetone, methyl ethyl ketone, diethyl ketone, methyl isobutyl ketone, and diisobutyl ketone to the residue after the organic solvent is removed by distillation, and then precipitating the metal sulfinate under cooling.

* * * * *